United States Patent [19]

Tvedt et al.

[11] Patent Number: 4,499,670
[45] Date of Patent: Feb. 19, 1985

[54] DEVICE FOR HANDLING THIN SECTIONS, IN PARTICULAR CRYOSECTIONS, AND PROCESS FOR FREEZE-DRYING THIN SECTIONS

[75] Inventors: Kare E. Tvedt, Trondheim; Guennar Kopstad, Tiller; Olav A. Haugen, Trondheim, all of Norway

[73] Assignee: C. Reichert Optische Werke, AG, Vienna, Austria

[21] Appl. No.: 504,011

[22] Filed: Jun. 13, 1983

[51] Int. Cl.$^3$ .............................. F26B 9/04; B30B 7/00
[52] U.S. Cl. ........................................ 34/143; 100/233
[58] Field of Search ................... 34/143, 145; 100/92, 100/93 P, 233

[56] References Cited

U.S. PATENT DOCUMENTS

| | | | |
|---|---|---|---|
| 2,501,922 | 3/1950 | Sutton | 34/143 |
| 3,199,221 | 8/1965 | Mehrlich et al. | 34/145 |
| 3,302,303 | 2/1967 | Aupoix | 34/145 |
| 4,083,205 | 4/1978 | Clarke et al. | 100/233 |

Primary Examiner—John J. Camby
Attorney, Agent, or Firm—Alan H. Spencer; Stephen Raines

[57] ABSTRACT

A handling device for thin sections, in particular cryosections, which serves as a multifunctional device for transferring, pressing, and holding the thin sections. The device possesses a holder for at least one carrier grid, this holder comprising a base plate and a positively-guided cover plate which can be moved onto the base plate. In addition, means are provided for the purpose of clamping the cover plate against the base plate and hence against a thin section which is present on the carrier grid. A separate holder plate is preferably detachably located in the base plate, the carrier grid being permanently attached to this holder plate, which is matched, in shape and dimensions, to the specimen holder of an electron microscope.

7 Claims, 6 Drawing Figures

DEVICE FOR HANDLING THIN SECTIONS, IN PARTICULAR CRYOSECTIONS, AND PROCESS FOR FREEZE-DRYING THIN SECTIONS

BACKGROUND OF THE INVENTION

The invention relates to a device for handling thin sections, in particular cryosections. The invention is further concerned with a process for freeze-drying sections of this nature.

In order to examine, in the electron microscope, organic preparations in the form of thin sections (cryosections) which are kept at low temperatures and are obtained by means of ultramicrotomes, it is necessary to subject the cryosections to a preliminary treatment which is designed to render them suitable for examination. This preliminary treatment calls for a pressing operation, followed by a freeze-drying operation and cautious warming to room temperature. For this purpose, the cryosections must firstly be transferred from the cold chamber of the ultramicrotome into a pressing appliance from which they are then brought, in turn, into a freeze-drying chamber. After the freeze-drying operation and warming to room temperature, they are then picked up and secured in the electron microscope by means of a holder. Small carrier grids are used for transporting the cryosections, these grids being made of carbon or beryllium. The cryosections, removed directly from the knife of the ultramicrotome, for example, by means of a hair, are transferred onto these carrier grids which must, due to their small size, be handled by means of tweezer-like tools. The operation of pressing the cryosections against the carrier grids is carried out with the aid of weights which possess polished surfaces.

When employing this known procedure, it is impossible, during the various operations, to prevent cryosections from being lost, becoming unusable, or, at least, being adversely affected to such an extent as to be of only limited suitability for examination by electron microscopy. First of all, during the operation of removing the carrier grid, and the cryosection present thereon, from the cold chamber of the microtome, there is a danger of the cryosection falling from the carrier grid as a result of the draught of air accompanying this operation. Furthermore, due to its very low mass, the carrier grid heats up very rapidly in the course of its short journey to the pressing tool, as a result of which the cryosection is also warmed prematurely, and is thereby adversely affected. During the operation of mounting the carrier grids in the pressing appliance and, also, later, in the receiving fixture of an electron microscope - following freeze-drying and warming - there is always the danger that contaminants will reach the preparation as a result of handling. Moreover, the pressing tools must be kept most scrupulously clean, in order to prevent the cryosections from being contaminated and, as a result, becoming unusable. Finally, during the course of the drying operation, it is almost impossible to prevent the cryosections from losing their initially flattened shape and becoming domed.

These disadvantages lead to the situation in which, despite the existence of very good, easily-operated ultramicrotomes, the preparation of cryosections for examination by electron microscopy has not yet become a routine operation, but is a matter for highly-specialized personnel, and even such specialists are not spared a comparatively high spoilage rate.

OBJECTS OF THE INVENTION

An object of the present invention is accordingly to provide a device by means of which the preparation of cryosections for electron-microscopic examination can be carried out in a manner such that there is no need for the exercise of exceptional care.

A further object is to reduce the spoilage rate quite considerably, or to avoid spoilage altogether.

BRIEF DESCRIPTION OF THE INVENTION

According to the present invention there is provided a device for handling thin sections, having a carrier grid for receiving a thin section, and a holder for the carrier grid, said holder comprising a base plate, a guided cover plate which can be moved onto said base plate, and means for clamping the cover plate against the base plate and hence against a thin section which is present on the carrier grid.

The device can be installed in the cold chamber of the ultramicrotome, in which a cryosection is produced, in a manner such that the cryosection, which is adhering to the knife of the ultramicrotome, can be transferred directly onto the carrier grid. The cover plate is thereupon guided against the base plate, and clamped, so that the cryosection which is present on the carrier grid is pressed firmly onto it. The device, in its closed form, can now be removed from the cold chamber, there being no possibility of the loss of the cryosection.

As a result of the clamping of the cover plate and base plate, the cryosection will, moreover, already have been pressed flat, so that it is unnecessary to transfer it to a separate pressing appliance. Rather, the thin section can immediately be placed in the freeze-drying chamber. For this reason, and because the holder, compared to the carrier grid, possesses a considerably higher heat capacity, absolutely no undesired warming of the thin section occurs, since the carrier grid is substantially protected from the effect of the ambient temperature.

An important and independent feature of the invention is that, in the holder according to the invention, the operation of freeze-drying the cryosection is carried out with the latter in its pressed state. Since it is comparatively easy to store the holder complete, in the freeze-drying chamber, in a manner such that heat transfer proceeds only very slowly, it is possible to control the increase in the temperature of the cryosection in such a way that absolutely no adverse effect results. Moreover, for this reason, the cryosection retains its flattened shape, even after the cover plate has been lifted off, so that the examination in the electron microscope is not impeded.

According to a specially advantageous embodiment of the invention, the carrier grid, or carrier grids, is or are permanently attached to a holder plate which is detachably located in a recess in the base plate. This holder plate is preferably matched, in its dimensions and its shape, to the receiving fixture for the specimen holder of an electron microscope, in a manner such that it can be inserted directly into this fixture. It is accordingly unnecessary, following freeze-drying and re-warming, to handle the small carrier grid with the cryosection present thereon. Such handling has, in the past, given rise to difficulties and, frequently, to contamination. In accordance with the invention it is now possible to mount the comparatively large holder plate directly in the receiving fixture of the electron microscope, without any manipulation of the carrier grid or of the cryosection which is present on it.

In the course of the known procedure, instances have commonly occurred in which the cryosections have been lost because they have not remained on the carrier grid during the operation of pressing them flat, but have adhered to the pressing tool and have either fallen from this tool, or have been damaged while being detached from it. According to a further embodiment of the invention, it is also possible to eliminate this source of loss. This is achieved by an arrangement whereby an identical holder plate, with a carrier grid permanently attached to it, is located in the cover plate of the holder, in a manner such that, when the holder is in the clamped state, the thin section is held between the two carrier grids. The device accordingly presses the thin section flat, between the two grids, and it is immaterial on which of the two carrier grids it remains, for on account of the identical configuration of the two holder plates, it is possible to insert into the electron microscope that plate which carries the carrier grid to which the thin section is adhering.

In accordance with a special embodiment, the carrier grid is fastened, for example, by an adhesive, above an opening which extends through the holder plate, and a pressure element is located in the recess in the base plate. The holder plate can be fitted in the recess, and the pressure element projects into the opening and is in contact with the under surface of the carrier grid. This configuration promotes the freeze drying since the thin section is in communication with the environment, through the carrier grid. If, moreover, the height of the pressure element is adjustable, as is provided in accordance with a further embodiment, it is possible to set a defined optimum pressure for the operation of pressing the thin section flat.

The invention also provides a method for freeze-drying thin sections which comprises producing a thin section by a microtome, conveying said section onto a carrier grid, pressing said section flat, transferring said section together with said carrier grid into a freeze-drying chamber, and freeze drying said section in said chamber.

BRIEF DESCRIPTION OF THE DRAWINGS

Further advantages and features of the present invention are evident from the description, in the text which follows, of preferred illustrative embodiments, which refers to the drawings. In the drawings.

DETAILED DESCRIPTION OF THE INVENTION

Figure 1:
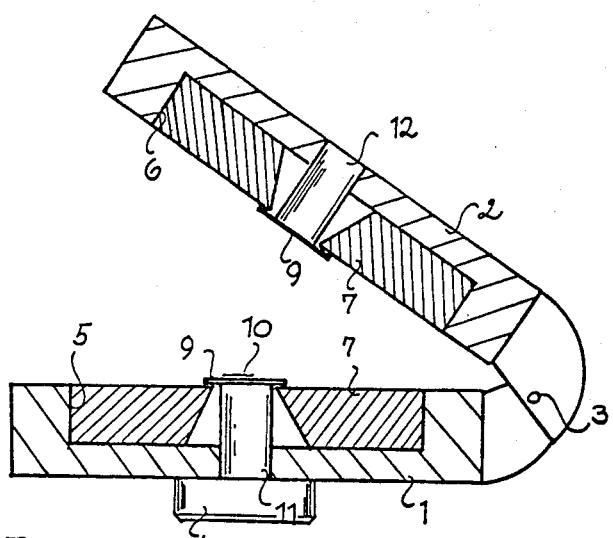
FIG. 1 shows a first embodiment of a handling device according to the invention, in the opened state, ready to receive a cryosection.
Figure 2:
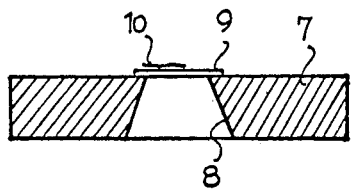
FIG. 2 shows a holder plate, represented on its own.
Figure 3:
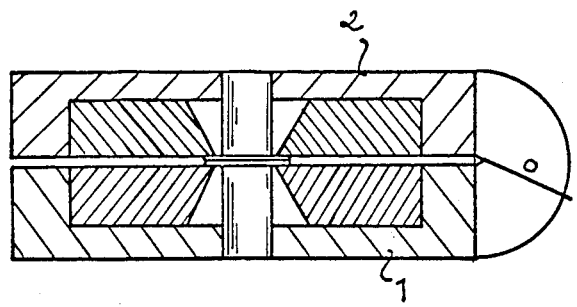
FIG. 3 shows the handling device according to FIG. 1, in the state in which it is acting as a pressing device.

The first embodiment of the handling device, according to the invention, represented in FIGS. 1 to 3, essentially comprises a base plate 1 and a cover plate 2, which are coupled together, by means of a hinge 3, to form a unit resembling a pair of jaws. The two plates 1, 2 are essentially symmetrical with respect to their upper surfaces, which face each other, have an elongated rectangular shape (directed perpendicularly to the plane of the drawing), and have, on their two opposite end faces, clamping screws 4 which enable them to be clamped together.

Each of the two plates 1, 2 possesses a rectangular recess 5 and 6, respectively, in which a holder plate 7 is secured in a manner permitting easy detachment. Screws can be employed for securing the holder plates 7, or they can be secured by snapping them in, behind springs (not shown) which project from the sidewalls of the recesses 5, 6.

In its center each of the holder plates 7 has at least one opening 8 which extends through the holder plate and widens towards the bottom of the associated recess 5, 6. Each opening 8 is covered, at its upper end, by a carrier grid 9, made of carbon or beryllium. The carrier grid 9 is glued to the upper surface of the holder plate. The thickness of the holder plate 7 is chosen, in relation to the associated recesses 5, 6, such that the carrier grids 9 come into precise contact with each other when the device is in the closed state (compare FIG. 3), and bear against each other under a pressure which depends on the pressure level which is preset. Spectroscopically pure graphite is preferably used as the material for the holder plate 7.

The device shown in FIGS. 1 to 3 is manipulated as follows:

Following the operation in which a cryosection is sliced, in an ultramicrotome, from a solid preparation block, the cryosection is transferred from the knife of the ultramicrotome onto the device, according to the invention, which is placed immediately beside the ultramicrotome. Stated more precisely, the cryosection is transferred onto the carrier grid 9 of the base plate 1, this transfer operation being carried out, for example, by means of a hair or some other known tool. In FIG. 2, the cryosection is marked 10. Thereafter, the cover plate 2 is swung downwards, about the hinge 3, so that the upper carrier grid 9 is pressed against the cryosection 10, which is clamped between the two carrier grids 9. By tightening the screws 4, which are supported on the plates 1, 2, if appropriate, by means of springs, which are not shown, it is possible to generate a clamping force which exerts a defined pressure on the cryosection 10 between the carrier grids 9. It is possible to tighten these screws 4 while the device is still inside the cold chamber of the ultramicrotome, or, alternatively, after it has been removed from this chamber. It is now possible to introduce the device, together with the cryosection, into a freze-drying chamber, without an undesired increase in temperature. The cryosection, in the pressed state inside the device, is freeze dried in the freeze-drying chamber and is warmed to room temperature in accordance with a defind temperature/time curve, the details of which, being well known in the art, are not given here. Following the freeze-drying operation the device is reopened by lifting the cover plate 2 from the base plate 1, and that holder plate 7 which has the cryosection 10 on its carrier grid 9 is removed from the device. Since, as hereinbefore described, the holder plate 7 is matched, in shape and dimensions, to the specimen holders of an electron microscope, in a manner which enables it to be secured directly inside these holders, there is no need to remove the cryosection 10 from the carrier grids 9. Rather, the holder plate 7 is itself transferred directly into the specimen holder of the electron microscope.

Following this procedure, the cryosection 10 proves, in virtually all cases, to be flat, due to the fact that the freeze-drying operation was carried out with the cryosection in the pressed state. The possibility of disadvantageous effects resulting from the deformation of the background, or from obstruction of the X-ray radiation by portions of the preparation which have domed up, is thus avoided.

The handling procedure described above indicates that the device, according to the invention, serves as a multifunctional device which transfers, presses, and holds the cryosection. On the one hand, the device possesses dimensions which enable it to be secured inside the cold chamber of the ultramicrotome, near its knife, in order to receive the cryosection from this knife. On the other hand, its dimensions are such that it can be manipulated directly by hand and without special care.

In the ullustrative embodiment represented, the holder plates 7 are inserted into the associated recesses 5, 6 in the plate 1, 2 in a manner such that a pressure element 11 or 12 projects from the bottom of the associated recess into the conical opening 8. The height of this pressure element 11, 12 is chosen to be such that its upper end face comes to bear directly against the undersurface of the carrier grid 9. During the pressing operation, each of the two carrier grids 9 is consequently supported against the associated pressure element so that a defined pressure is exerted on the cryosection 10 which is present between them. In the illustrative embodiment shown, the pressure elements 11, 12 are securely pressed into the associated plates 1,2. However, in place of these elements 11,12, set screws could be used. The set screws could be operated from the outside, thus enabling the contact pressure to be adjusted.

Figure 4:
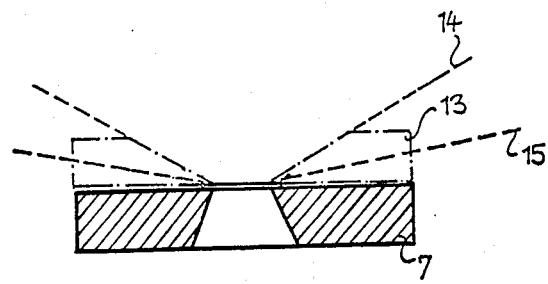
FIG. 4 shows a holder plate, represented on its own, which is mounted in the electron microscope, this Figure displaying the better accessibility of a thin section present on this holder plate compared to the known procedure.

FIG. 4 shows the arrangement of a holder plate 7 in the electron microscope. In the course of an X-ray analysis in the electron microscope, shadowing occurs as a result of the lateral arrangement of the X-ray detector and the special device 13 for holding the carrier grid, this device, necessary up to now, being represented—as the state of the art—only by dash-dot lines. Due to this shadowing, it has been necessary, up to now, to tilt the device for holding the cryosection through an angle corresponding to the broken line 14. In contrast, the device 13 for holding the carrier grid is rendered unnecessary by the procedure, according to the invention. From this, the angle of tilt which is required in order to obtain a suitable signal proves to be considerably smaller, and corresponds to the broken line 15.

Figure 5:
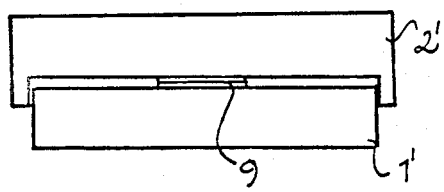
FIGS. 5 and 6 show second and third embodiments of the handling device according to the invention.
Figure 6:
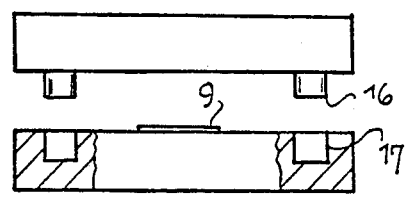

FIGS. 5 and 6 show modified embodiments of the device, according to the invention, in which the hinge 3 between the plates 1, 2 is replaced by making the cover plate 2' a sliding fit on the external surface of the base plate 1' (FIG. 5), or, alternatively, by means of a pinhole fit, in which locating pins 16 move into locating holes 17 during the closing movement. The positive guidance of the plates towards each other eliminates any excessive relative movement parallel to the carrier grid 9 during the pressing operation, such movement being capable of damaging the cryosection 10 which is present on the carrier grid.

The device according to the invention consequently possesses the advantages not only that the preparation of cryosections for electron-microscopic examination can be carried out simply and without excessive care being required, but also that the number of cryosections which can be used for the examination is considerably increased, that there is no danger of the delicate carrier grids being damaged or contaminated, and that the rewarming of the cryosections to room temperature can take place in a controlled manner, during the freezedrying operation, from the original temperature of, for example, $-120°$ C. This is effected by, for example, mounting the base plate 1 on sharp points, which substantially minimize the thermal contact with respect to the support and thereby prevent disturbing changes from occurring in the cryosections as a result of excessively rapid warming.

Instead of the clamping means which are installed directly on the plates 1, 2 themselves, and which generate the contact pressure for the cryosection 10, it is also possible to insert the plates 1, 2, especially those according to FIGS. 5 and 6, into a separate clamping appliance, and to press them together.

We claim:

1. A device for handling thin sections, having a carrier grid for receiving a thin section, and a holder for the carrier grid, said holder comprising a baseplate, a holder-plate detachably located in a recess in said baseplate, said carrier grid being fastened above an opening which extends through said holder-plate, a pressure element located in the recess in said baseplate, said pressure element projecting into said opening into contact with the undersurface of the carrier grid, a guided cover plate which can be moved onto said baseplate, and means for clamping the cover plate against the baseplate and hence against a thin section which is present on the carrier grid.

2. A device according to claim 1, wherein said carrier grid is permanently attached to said holder-plate, and another holder plate located in said cover plate, another carrier grid being permanently attached to said another holder-plate, said another holder plate wherein the thin section is held between said carrier grid and said another carrier grid when said device is in the clamped state.

3. A device according to claim 1 wherein said pressure element comprises adjustment means whereby the height of said pressure element relative to said base plate is adjustable.

4. A device according to claim 1 wherein said holder plate is dimensioned and arranged to be received in the receiving fixture of an electron microscope.

5. A device according to claim 1 wherein said holder plate is composed of high-purity graphite.

6. A device according to claim 1 further comprising hinge means coupling together said base plate and said cover plate.

7. A device according to claim 1 further comprising guide means for slidably guiding said base plate positively relative to said cover plate.

* * * * *